United States Patent [19]

Downing et al.

[11] Patent Number: 5,552,411
[45] Date of Patent: Sep. 3, 1996

[54] SULFONYLQUINOLINES AS CENTRAL NERVOUS SYSTEM AND CARDIOVASCULAR AGENTS

[75] Inventors: Dennis M. Downing; Jonathan L. Wright, both of Ann Arbor, Mich.

[73] Assignee: Warner-Lambert Company, Morris Plains, N.J.

[21] Appl. No.: 452,047

[22] Filed: May 26, 1995

[51] Int. Cl.⁶ ......................... A61K 31/47; C07D 215/36
[52] U.S. Cl. ............................. 514/312; 546/172
[58] Field of Search ............................ 514/312; 546/172

[56] References Cited

PUBLICATIONS

Lewis, SJ, Mirrlees MS, Taylor PJ. (1983). Quant. Struct. Act. Relat. Pharmacol., Chem. Biiol. 2(3), 100–11 (Abstract).
Gilman et al., *J. Am. Chem. Soc.*, 66:1577–1579 (1946).

*Primary Examiner*—C. Warren Ivy
*Assistant Examiner*—Evelyn Huang
*Attorney, Agent, or Firm*—Francis J. Tinney

[57] ABSTRACT

Sulfonylquinolines are described, as well as methods for the preparation and pharmaceutical composition of same, which are useful as central nervous system agents and are particularly useful as antiobesity agents and for the treatment of hypertension.

10 Claims, No Drawings

SULFONYLQUINOLINES AS CENTRAL NERVOUS SYSTEM AND CARDIOVASCULAR AGENTS

BACKGROUND OF THE INVENTION

The present invention relates to novel substituted sulfonylquinolines useful as pharmaceutical agents, to methods for their production, to pharmaceutical compositions which include these compounds and a pharmaceutically acceptable carrier, and to pharmaceutical methods of treatment. The novel compounds of the present invention are neuropeptide Y antagonists useful for the treatment of obesity and hypertension.

Neuropeptide Y (NPY) is involved in the control of feeding in mammals. Administration of neuropeptide Y into the central nervous system causes a dramatic increase in feeding in rats and based on the activity of fragments of the NPY molecule, this effect appears to be mediated by the $Y_1$ subtype of NPY receptor (Dryden S., Frankish H., Wang Q., and Williams G. Neuropeptide Y and energy balance: one way ahead for the treatment of obesity? *Eur. J. Clin. Invest.*, 1994;24:293–308). The compounds of the present invention are neuropeptide $Y_1$ antagonists and are useful in the treatment of obesity.

Neuropeptide Y is also involved in the regulation of blood pressure. Neuropeptide Y antagonists have been shown to be effective antihypertensive agents (Edvinsson L., Hakanson R., Wahlestedt C., and Uddman R. Effects of Neuropeptide Y on the cardiovascular system. *Trends Pharmacol. Sci.*, 1987;8:231–235). The compounds of the present invention are neuropeptide Y antagonists and are useful in the treatment of hypertension.

We have surprisingly and unexpectedly found that a series of sulfonylquinolines are neuropeptide Y antagonists which bind selectively to the neuropeptide $Y_1$ receptor subtype and are thus useful as antiobesity and antihypertensive agents.

SUMMARY OF THE INVENTION

Accordingly, the present invention is a compound of Formula I

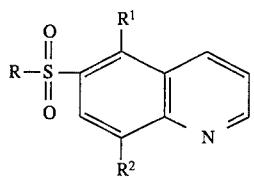

wherein R is aryl, or heteroaryl;
$R^1$ is —$NO_2$,
—CN,
—$CO_2R^3$ wherein $R^3$ is H,
alkyl, or
aryl,
—$SO_2R^3$ wherein $R^3$ is as defined above,

wherein $R^3$ is as defined above, or

wherein $R^3$ is as defined above;
$R^2$ is —$NH_2$,
—OH, or
—SH; with the exclusion of

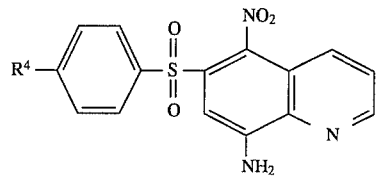

wherein $R^4$ is —$NH_2$ or

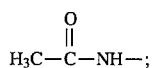

or
a pharmaceutically acceptable salt thereof.

As antagonists of neuropeptide Y, the compounds of Formula I are antiobesity agents. They are also useful for the treatment of hypertension.

A still further embodiment of the present invention is a pharmaceutical composition for administering an effective amount of a compound of Formula I in unit dosage form in the treatment methods mentioned above. Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

"Alkoxy" and "thioalkoxy" are O-alkyl or S-alkyl of from 1 to 6 carbon atoms as defined above for "alkyl".

The term "aryl" means an aromatic radical which is a phenyl group, a 1- or 2-naphthyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, N-acetylamino, cyano or nitro, or a 1- or 2-naphthyl group substituted by 1 to 4 substituents as defined above for a phenyl group substituted by 1 to 4 substituents.

The term "heteroaryl" means a heteroaromatic radical which is 2-, 3-, or 4-pyridinyl, 2-, 4-, or 5-pyrimidinyl, 2-, or 3-thienyl, 2-, 3-, 4-, 5-, 6-, 7-, or 8-quinolinyl, or 2or 5-pyrimidinyl, 2-, or 3-thienyl, 2-, 3-, 4-, 5-, 6-, 7-, or 8-quinolinyl substituted by 1 to 3 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, N-acetylamino, cyano or nitro.

"Halogen" is fluorine, chlorine, bromine, or iodine.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenylsubstituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma. Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma. Sci.*, 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center my exist in the R(D) or S(L) configuration. The present invention includes all enantiomeric and epimeric forms as well as the appropriate mixtures thereof.

A preferred compound of Formula I is one wherein

R is phenyl,
phenyl substituted by 1 to 4 substituents selected from the group consisting of:
alkyl,
alkoxy,
thioalkoxy,
hydroxy,
halogen,
trifluoromethyl,
amino,
alkylamino
dialkylamino,
N-acetylamino,
cyano or nitro,
1- or 2-naphthyl,
2-, 3-, or 4-pyridinyl, or
2-, 3-, 4-, 5-, 6-, 7-, or 8-quinolinyl;
$R^1$ is $-NO_2$;
$R^2$ is $-NH_2$.

Particularly valuable are:
6-Benzenesulfonyl-5-nitro-quinolin-8-ylamine;
6-(4-Chloro-benzenesulfonyl)-5-nitro-quinolin- 8-ylamine;
6-(4-Methoxy-benzenesulfonyl)-5-nitro-quinolin-8-ylamine;
5-Nitro-6-(toluene-4-sulfonyl)-quinolin-8-ylamine;
6-(Naphthalene-2-sulfonyl)-5-nitro-quinolin-8-ylamine;
6-(2,5-Dimethyl-benzenesulfonyl)-5-nitro-quinolin-8-ylamine;
6-(4-tert-Butyl-benzenesulfonyl)-5-nitro-quinolin-8-ylamine;
5-Nitro-6-(4-nitro-benzenesulfonyl)-quinolin-8-ylamine;
5-Nitro-6-(toluene-3-sulfonyl)-quinolin-8-ylamine;
4-(8-Amino-5-nitro-quinoline-6-sulfonyl)-phenol;
4-(8-Amino-5-nitro-quinoline-6-sulfonyl)-benzonitrile;
5-Nitro-6-(toluene-2-sulfonyl)-quinolin-8-ylamine;
6-(2-Chloro-benzenesulfonyl)-5-nitro-quinolin- 8-ylamine;
6-(2,6-Dimethyl-benzenesulfonyl)-5-nitro-quinolin-8-ylamine;
6-(3-Chloro-benzenesulfonyl)-5-nitro-quinolin- 8-ylamine;
6-(4-Fluoro-benzenesulfonyl)-5-nitro-quinolin- 8-ylamine;
6-(3-Methoxy-benzenesulfonyl)-5-nitro-quinolin-8-ylamine;
6-(2-Ethyl-benzenesulfonyl)-5-nitro-quinolin-8-ylamine;
6-(2-Isopropyl-benzenesulfonyl)-5-nitro-quinolin-8-ylamine;
6-(Naphthalene-1-sulfonyl)-5-nitro-quinolin-8-ylamine;
6-(2-Methoxy-benzenesulfonyl)-5-nitro-quinolin-8-ylamine;
6-(2,4-Dimethyl-benzenesulfonyl)-5-nitro-quinolin-8-ylamine;
6-(2,6-Dichloro-benzenesulfonyl)-5-nitro-quinolin-8-ylamine;
6-(2-Bromo-benzenesulfonyl)-5-nitro-quinolin-8-ylamine;
N-[2-(8-Amino-5-nitro-quinoline-6-sulfonyl)-phenyl]-acetamide;
6-(2,3-Dichloro-benzenesulfonyl)-5-nitro-quinolin-8-ylamine;
6-(2-Fluoro-benzenesulfonyl)-5-nitro-quinolin- 8-ylamine;
6-(2,6-Diisopropyl-benzenesulfonyl)-5-nitro-quinolin-8-ylamine;
5-Nitro-6-(2-trifluoromethyl-benzenesulfonyl)-quinolin-8-ylamine;
6-(2,5-Dichloro-benzenesulfonyl)-5-nitro-quinolin-8-ylamine; and 6-(2-tert-Butyl-benzenesulfonyl)-5-nitro-quinolin-8-ylamine;

or a pharmaceutically acceptable salt thereof.

The compounds of Formula I are valuable neuropeptide $Y_1$ antagonists. The compounds of Formula I were tested for their ability to bind to the neuropeptide $Y_1$ receptor subtype as measured by their inhibition of [$^{125}$I]Peptide YY to human $NPY_1$ receptors.

Binding Assay Protocol

Preparation of Cells and Cell Membranes

Human neuroblastoma cells, SK-N-MC, obtained from American Type Culture Collection were grown in Dulbecco's modified Eagle medium (Gibco) containing 10% fetal bovine serum and 100 units per mL/100 µg/mL penicillin/streptomycin (Gibco). After cells were confluent, growth media was replaced with fresh media and cells were allowed to continue growing for an additional 24 hours. Cells were then harvested in a buffer consisting of the following: 25 mM Tris(hydroxymethyl)amino methane (Tris), pH 7.4, 6 mM $MgCl_2$, 250 µg/mL bacitracin, 250 µg/mL aprotinin, 250 µg/mL leupeptin, 250 µg/mL 4-(2-aminoethyl)-benzenesulfonylfluoride hydrochloride (Pefabloc) (Pentapharm AG). Growth media was removed and cells were lifted from the flasks with Dulbecco's phosphate buffered saline (D-PBS) containing 0.02% ethylenediaminetetraacetic acid (EDTA). Cells were pelleted and homogenized using a polytron, and broken membranes were pelleted by centrifugation at 18,000 rpm for 10 minutes at 4° C. The pelleted membranes were resuspended in the above buffer and frozen at ×70° C.

Assay Protocol

D-PBS (Gibco) pH 7.4, containing 0.5 g/L bacitracin and 1 g/n bovine serum albumin (BSA), was used in the preparation of compound and radiolabel. Each assay tube consisted of the following: 100 µn of compound or buffer, 100 µL[$^{125}$I]-PYY (Peptide YY) (30 pM), and 50 µL SK-N-MC preparation containing 50 µg/tube membrane protein for a total volume of 250 µL/tube. Non-specific binding was defined by the addition of 300 nM final concentration of neuropeptide Y. After addition of all reagents, tubes were shaken while incubating for 60 minutes at room temperature. The assay was terminated by filtering through a Whatman GF/C filter previously saturated with 0.1% polyethylenimine in 10 mM Tris, pH 7.5 containing 0.1% BSA. Filters were punched from the filter mat, placed in tubes, and counted for 1 minute using a gamma counter. The $K_i$ was determined using the Graph PAD data analysis software program.

NPY cAMP Method

Activation of the $NPY_1$ receptor in SK-N-MC cells is followed by a lowering of cAMP levels. When cAMP levels are elevated by the adenylyl cyclase activator forskolin, this forskolin-stimulated rise in cAMP is inhibited via activation of the $NPY_1$ receptors by $NPY_1$. $NPY_1$ antagonists, which occupy $NPY_1$ receptors without activating them, would have no effect by themselves on forskolin-stimulated cAMP responses and would reverse NPY inhibition of the forskolin-elevated cAMP levels.

This inhibition would be surmountable by competing off the antagonist with increasing concentrations of NPY. The result of the $NPY_1$ antagonist would be to increase the $EC_{50}$ for NPY inhibition of forskolin-stimulated cAMP.

Assay Protocol

SK-N-MC cells were grown to confluency in Dulbecco's modified Eagle medium (Gibco) containing 10% fetal bovine serum and 100 units per mn/100 µg/mL penicillin/streptomycin (Gibco). On the day of the experiment, cells were washed with serum and antibiotic-free medium containing 1 mM IBMX (a cAMP phosphodiesterase inhibitor). Compound (10 µM) or vehicle was added to each well. Following a 5-minute incubation at room temperature, vehicle or various concentrations of NPY was added. Following a 20-minute incubation at 37° C., 10 µM forskolin (an adenylyl cyclase activator) or vehicle was added. After an additional 20-minute incubation at 37° C., the assay was terminated by adding 0.5 mL of 0.5% trichloroacetic acid. The samples were rotated for 1 hour at room temperature, and the acidified medium was assayed for cAMP by the Amersham SPA kit.

The data in Table 1 show the neuropeptide Y receptor binding activity of representative compounds of Formula I. Table 2 shows that selected compounds of Formula I behave as antagonists at the $NP_1$ receptor.

TABLE 1

Receptor Binding of Compounds of Formula I

| Example Number | Compound | Inhibition of [$^{125}$I]Peptide YY Binding to Human Neuropeptide $Y_1$ Receptors $K_i$, nM |
|---|---|---|
| 1 | 6-Benzenesulfonyl-5-nitro-quinolin-8-ylamine | 297 |
| 2 | 6-(4-Chloro-benzenesulfonyl)-5-nitro-quinolin-8-ylamine | 1750 |
| 3 | 6-(4-Methoxy-benzenesulfonyl)-5-nitro-quinolin-8-ylamine | 1135 |
| 4 | 5-Nitro-6-(toluene-4-sulfonyl)-quinolin-8-ylamine | 594 |
| 5 | 6-(Naphthalene-2-sulfonyl)-5-nitro-quinolin-8-ylamine | 1200 |
| 6 | 6-(2,5-Dimethyl-benzenesulfonyl)-5-nitro-quinolin-8-ylamine | 148 |
| 7 | 6-(4-tert-Butyl-benzenesulfonyl)-5-nitro-quinolin-8-ylamine | 3200 |
| 8 | 5-Nitro-6-(4-nitro-benzenesulfonyl)-quinolin-8-ylamine | 1000 |
| 9 | 5-Nitro-6-(toluene-3-sulfonyl)-quinolin-8-ylamine | 373 |
| 10 | 4-(8-Amino-5-nitro-quinoline-6-sulfonyl)-phenol | 136 |
| 11 | 4-(8-Amino-5-nitro-quinoline-6-sulfonyl)-benzonitrile | 854 |
| 12 | 5-Nitro-6-(toluene-2-sulfonyl)-quinolin-8-ylamine | 119 |
| 13 | 6-(2-Chloro-benzenesulfonyl)-5-nitro-quinolin-8-ylamine | 93 |
| 14 | 6-(2,6-Dimethyl-benzenesulfonyl)-5-nitro-quinolin-8-ylamine | 295 |
| 15 | 6-(3-Chloro-benzenesulfonyl)-5-nitro-quinolin-8-ylamine | 892 |
| 16 | 6-(4-Fluoro-benzenesulfonyl)-5-nitro-quinolin-8-ylamine | 603 |
| 17 | 6-(3-Methoxy-benzenesulfonyl)-5-nitro-quinolin-8-ylamine | 311 |
| 18 | 6-(2-Ethyl-benzenesulfonyl)-5-nitro-quinolin-8-ylamine | 129 |
| 19 | 6-(2-Isopropyl-benzenesulfonyl)-5-nitro-quinolin-8-ylamine | 48 |
| 20 | 6-(Naphthalene-1-sulfonyl)-5-nitro-quinolin-8-ylamine | 46 |
| 21 | 6-(2-Methoxy-benzenesulfonyl)-5-nitro-quinolin-8-ylamine | 490 |
| 22 | 6-(2,4-Dimethyl-benzenesulfonyl)-5-nitro-quinolin-8-ylamine | 222 |

TABLE 1-continued

Receptor Binding of Compounds of Formula I

| Example Number | Compound | Inhibition of [$^{125}$I]Peptide YY Binding to Human Neuropeptide $Y_1$ Receptors $K_i$, nM |
|---|---|---|
| 23 | 6-(2,6-Dichloro-benzenesulfonyl)-5-nitro-quinolin-8-ylamine | 273 |
| 24 | 6-(2-Bromo-benzenesulfonyl)-5-nitro-quinolin-8-ylamine | 234 |
| 25 | N-[2-(8-Amino-5-nitro-quinoline-6-sulfonyl)-phenyl]-acetamide | 590 |
| 26 | 6-(2,3-Dichloro-benzenesulfonyl)-5-nitro-quinolin-8-ylamine | 93 |
| 27 | 6-(2-Fluoro-benzenesulfonyl)-5-nitro-quinolin-8-ylamine | 58 |
| 28 | 6-(2,6-Diisopropyl-benzenesulfonyl)-5-nitro-quinolin-8-ylamine | 48 |
| 29 | 5-Nitro-6-(2-trifluoromethyl-benzenesulfonyl)-quinolin-8-ylamine | 84 |
| 30 | 6-(2,5-Dichloro-benzenesulfonyl)-5-nitro-quinolin-8-ylamine | 283 |
| 31 | 6-(2-tert-Butyl-benzenesulfonyl)-5-nitro-quinolin-8-ylamine | 1400 |

TABLE 2

Effect of Selected Compounds of Formula I[1] on the $EC_{50}$[2] of NPY-induced Inhibition of Forskolin-Stimulated cAMP Production in SK-N-MC Cells Transfected With the Human $NPY_1$ Receptor

| Example | Compound | NPY $EC_{50}$ nM |
|---|---|---|
| 13 | 6-(2-Chloro-benzenesulfonyl)-5-nitro-quinolin-8-ylamine | 6.6 |
| 19 | 6-(2-Isopropyl-benzenesulfonyl)-5-nitro-quinolin-8-ylamine | 8.2 |

[1]The compounds alone had no effect on forskolin-stimulated cAMP levels.
[2]NPY alone $EC_{50}$ = 0.3 nM A compound of Formula I

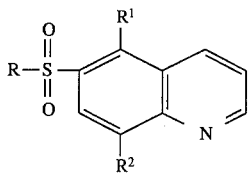

I wherein R is aryl, or heteroaryl;

$R^1$ is —$NO_2$,

—CN,

—$CO_2R^3$ wherein $R^3$ is H, alkyl, or aryl,

—$SO_2R^3$ wherein $R^3$ is as defined above,

wherein $R^3$ is as defined above, or $$-\underset{\underset{O}{\|}}{C}-R^3$$

wherein $R^3$ is as defined above;

$R^2$ is —$NH_2$,

—OH, or

—SH; with the exclusion of

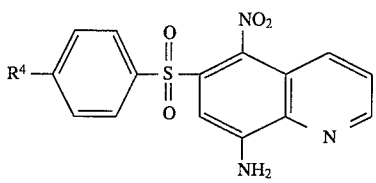

wherein $R^4$ is —$NH_2$ or $$H_3C-\underset{\underset{O}{\|}}{C}-NH-;$$

or a pharmaceutically acceptable salt thereof may be prepared by reaction of a compound of Formula II

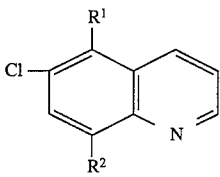

II wherein $R^1$ and $R^2$ are as defined above with a compound of Formula III

III wherein R is as defined above in a solvent such as, for example, ethylene glycol, diglyme and the like at about 100° C. to about 300° C. from about 1 hour to about 24 hours. Preferably, the reaction is carried out in ethylene glycol and diglyme at the reflux temperature of the solvent for 2 hours.

Alternatively, a compound of Formula I may be prepared via treatment of a compound of Formula IV

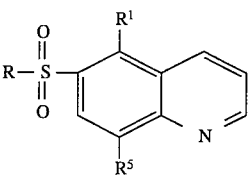

IV wherein $R^5$ is

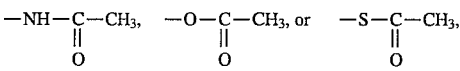

R and $R^1$ are as defined above with an acid such as, for example, hydrochloric acid and the like either neat or with a cosolvent such as, for example, dioxane and the like at about room temperature to about the reflux temperature of the mixture for about 30 minutes to about 6 hours. Preferably, the reaction is performed in 50% 2N hydrochloric acid and 50% dioxane at reflux temperature for 2 hours.

A compound of Formula IV may be prepared via oxidation of a compound of Formula V

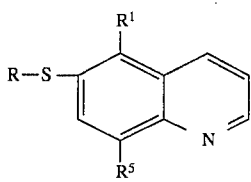

V wherein R, $R^1$, and $R^5$ are as defined above with an oxidant such as, for example, meta-chloroperoxybenzoic acid and the like in a solvent such as, for example, chloroform and the like at about room temperature to about the reflux temperature of the solvent for from about 1 hour to about 24 hours. Preferably, the reaction is carried out using meta-chloroperoxybenzoic acid in chloroform at the reflux temperature of the solvent for 18 hours.

A compound of Formula V may be prepared via reacting a compound of Formula II with a compound of Formula VI RSNa          VI wherein R is as defined above in a solvent such as, for example, tetrahydrofuran and the like at from about −20° C. to about 50° C. from about 15 minutes to about 6 hours. Preferably, the reaction is carried out in tetrahydrofuran at 0° C. for 2 hours.

Compounds II, III, and VI are either known or capable of being prepared by methods known in the art.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious o those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as antiobesity and antihypertensive agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

6-Benzenesulfonyl-5-nitro-quinolin-8-ylamine

A mixture of benzenesulfinic acid (0.24 g) is stirred in tetrahydrofuran (50 mL) and sodium hydride (0.06 g of 60% in oil) is added. The mixture is stirred at room temperature for 1 hour and the solvent evaporated. The residue is stirred in ethylene glycol (50 mL) and 2-methoxyethanol (50 mL) and 6-chloro-5-nitro-quinolin-8-ylamine (Gilman H., et al., *Journal of American Chemical Society*, 1946;66:1577) (0.34 g) are added. The mixture is stirred at reflux for 3 hours. Upon cooling, water (700 mL) is added and the precipitate collected. The solid is recrystallized from ethanol to give the title compound as a yellow solid; mp 211°–213° C.

In a process analogous to Example 1 using appropriate starting materials, the corresponding compounds of Formula I are prepared as follows:

EXAMPLE 2

6-(4-Chloro-benzenesulfonyl)-5-nitro-quinolin-8-ylamine; mp 181°–185° C.

EXAMPLE 3

6-(4-Methoxy-benzenesulfonyl)-5-nitro-quinolin-8-ylamine; mp 249°–250° C.

EXAMPLE 4

5-Nitro-6-(toluene-4-sulfonyl)-quinolin-8-ylamine; mp 226°–229° C.

EXAMPLE 5

6-(Naphthalene-2-sulfonyl)-5-nitro-quinolin-8-ylamine; mp 202°–206° C.

EXAMPLE 6

6-(2,5-Dimethyl-benzenesulfonyl)-5-nitro-quinolin-8-ylamine; mp 212°–216° C.

EXAMPLE 7

6-(4-ter-Butyl-benzenesulfonyl)-5-nitro-quinolin-8-ylamine; mp 262°–265° C.

EXAMPLE 8

5-Nitro-6-(4-nitro-benzenesulfonyl)-quinolin-8-ylamine; mp 254°–255° C.

EXAMPLE 9

5-Nitro-6-(toluene-3-sulfonyl)-quinolin-8-ylamine; mp 228°–230° C.

EXAMPLE 10

4-(8-Amino-5-nitro-quinoline-6-sulfonyl)-phenol; mp 238°–240° C.

EXAMPLE 11

4-(8-Amino-5-nitro-quinoline-6-sulfonyl)-benzonitrile; mp 248°–249° C.

EXAMPLE 12

5-Nitro-6-(toluene-2-sulfonyl)-quinolin-8-ylamine; mp 202°–205° C.

EXAMPLE 13

6-(2-Chloro-benzenesulfonyl)-5-nitro-quinolin-8-ylamine; mp 196°–198° C.

EXAMPLE 14

6-(2,6-Dimethyl-benzenesulfonyl)-5-nitro-quinolin-8-ylamine; mp 234°–237°C.

EXAMPLE 15

6-(3-Chloro-benzenesulfonyl)-5-nitro-quinolin-8-ylamine; mp 198°–203° C.

EXAMPLE 16

6-(4-Fluoro-benzenesulfonyl)-5-nitro-quinolin-8-ylamine; mp 216°–219° C.

EXAMPLE 17

6-(3-Methoxy-benzenesulfonyl)-5-nitro-quinolin-8-ylamine; mp 194°–195° C.

EXAMPLE 18

6-(2-Ethyl-benzenesulfonyl)-5-nitro-quinolin-8-ylamine

Step A: Preparation of N-[6-(2-Ethyl-phenylsulfanyl)-5-nitro-quinolin-8-yl]-acetamide Sodium hydride (0.09 g of 60% in oil) is added to 2-ethylthiophenol (0.26 g) in tetrahydrofuran (10 mL) and stirred for 15 minutes. N-(6-chloro-5-nitro-quinolin-8-yl)-acetamide (Gilman H., et al., *Journal of American Chemical Society*, 1946;66:1577) (0.5 g) is added and the mixture stirred at room temperature for 12 hours. The mixture is added to water (150 mL) and extracted with ethyl acetate (3×100 mL). The extracts are washed with saturated brine (150 mL), dried over magnesium sulfate, filtered, and evaporated to leave an oil. The oil is purified by chromatography on silica gel eluting with 50% ethyl acetate/hexane to give the title compound as a yellow solid.

Step B: Preparation of N-[6-(2-Ethyl-benzenesulfonyl)-5-nitro-quinolin-8-yl]-acetamide N-[6-(2-Ethyl-phenylsulfanyl)-5-nitro-quinolin-8-yl]-acetamide (0.48 g) and 3-chloroperoxybenzoic acid (1.16 g of 78%) in chloroform (20 mL) is stirred at reflux for 18 hours. The mixture is diluted with dichloromethane (200 mL) and washed with 2N sodium carbonate (200 mL), dried over magnesium sulfate, filtered, and evaporated to leave the title compound as a yellow solid.

step C: preparation of 6-(2-Ethyl-benzenesulfonyl)-5-nitro-quinolin-8-ylamine

N-[6-(2-Ethyl-benzenesulfonyl)-5-nitro-quinolin-8-yl]-acetamide (0.5 g) is stirred at reflux in 2N hydrochloric acid (50 mL) and 1,4-dioxane (50 mL) for 2 hours. The mixture is added to 2N sodium carbonate (200 mL) and extracted with ethyl acetate (3×100 mL). The extracts are washed with saturated brine (150 mL), dried over magnesium sulfate, filtered, and evaporated to leave an orange solid. This solid is crystallized from hot ethyl acetate to give the title compound as orange crystals; mp 213°–216° C.

In a process analogous to Example 18 using appropriate starting materials, the corresponding compounds of Formula I are prepared as follows:

EXAMPLE 19

6-(2-Isopropyl-benzenesulfonyl)-5-nitro-quinolin-8-ylamine; mp 218°–219° C.

EXAMPLE 20

6-(Naphthalene-1-sulfonyl)-5-nitro-quinolin-8-ylamine; mp 153°–156° C.

EXAMPLE 21

6-(2-Methoxy-benzenesulfonyl)-5-nitro-quinolin-8-ylamine; mp 244°–246° C.

EXAMPLE 22

6-(2.4-Dimethyl-benzenesulfonyl)-5-nitro-quinolin-8-ylamine; mp 199°–201° C.

EXAMPLE 23

6-(2,16Dichloro-benzenesulfonyl)-5-nitro-quinolin-8-ylamine; mp 262°–264° C.

EXAMPLE 24

6-(2-Bromo-benzenesulfonyl)-5-nitro-quinolin-8-ylamine; mp 243°–245° C.

EXAMPLE 25

N-[2-(8-Amino-5-nitro-quinoline-6-sulfonyl)-phenyl]-acetamide; mp 236°–238° C.

EXAMPLE 26

6-(2,3-Dichloro-benzenesulfonyl)-5-nitro-quinolin-8-ylamine; mp 212°–213° C.

EXAMPLE 27

6-(2-Fluoro-benzenesulfonyl)-5-nitro-quinolin-8-ylamine; mp 192°–194° C.

EXAMPLE 28

6-(2,6-Diisopropyl-benzenesulfonyl)-5-nitro-quinolin-8-ylamine; mp 260°–262° C.

EXAMPLE 29

5-Nitro-6-(2-trifluoromethyl-benzenesulfonyl)-quinolin-8-ylamine; mp 218°–220° C.

EXAMPLE 30

6-(2,5-Dichloro-benzenesulfonyl)-5nitro-quinolin-8-ylamine; mp 256°–258° C.

EXAMPLE 31

6-(2-tert-Butyl-benzenesulfonyl)-5-nitro-quinolin-8-ylamine; mp 260°–262° C.

We claim:
1. A compound of Formula I

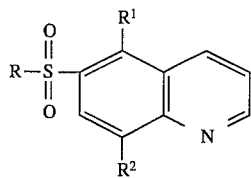

wherein R is aryl, or
R$^1$ is —NO$_2$,
—CN,
—CO$_2$ R$^3$ wherein R$^3$ is H alkyl, or aryl,
—SO$_2$R$^3$ wherein R$^3$ is as defined above

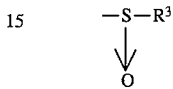

wherein R$^3$ is as defined above, or

wherein R$^3$ is as defined above;
R$^2$ is —NH$_2$,
—OH, or
—SH; with the exclusion of

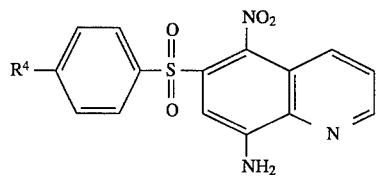

wherein R$^4$ is —NH$_2$ or

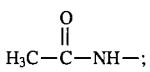

or a pharmaceutically acceptable salt thereof.
2. A compound according to claim 1 wherein R is phenyl, phenyl substituted by 1 to 4 substituents selected from the group consisting of:
alkyl,
alkoxy,
thioalkoxy,
hydroxy,
halogen,
trifluoromethyl,
amino,
alkylamino,
dialkylamino,
N-acetylamino,
cyano or nitro,
R$^1$ is —NO$_2$;
R$^2$ is —NH$_2$.
3. A compound according to claim 2 selected from the group consisting of:
6-Benzenesulfonyl-5-nitro-quinolin-8-ylamine;
6-(4-Chloro-benzenesulfonyl)-5-nitro-quinolin-8-ylamine;
6-(4-Methoxy-benzenesulfonyl)5-nitro-quinolin-8-ylamine;

5-Nitro-6-(toluene-4-sulfonyl)-quinolin-8-ylamine;
6-(Naphthalene-2-sulfonyl)-5-nitro-quinolin- 8-ylamine;
6-(2,5-Dimethyl-benzenesulfonyl)-5-nitro-quinolin-8-ylamine;
6-(4-tert-Butyl-benzenesulfonyl)-5-nitro-quinolin-8-ylamine;
5-Nitro-6-(4-nitro-benzenesulfonyl)-quinolin-8-ylamine;
5-Nitro-6-(toluene-3-sulfonyl)-quinolin-8-ylamine;
4-(8-Amino-5-nitro-quinoline-6-sulfonyl)-phenol;
4-(8Amino-5-nitro-quinoline-6-sulfonyl)-benzonitrile;
5-Nitro-6-(toluene-2-sulfonyl)-quinolin-8-ylamine;
6-(2-Chloro-benzenesulfonyl)-5-nitro-quinolin-8-ylamine;
6-(2,6-Dimethyl-benzenesulfonyl)-5-nitro-quinolin-8-ylamine;
6-(3-Chloro-benzenesulfonyl)-5-nitro-quinolin-8-ylamine;
6-(4Fluoro-benzenesulfonyl)-5-nitro-quinolin-8-ylamine;
6-(3-Methoxy-benzenesulfonyl)-5-nitro-quinolin8-ylamine;
6-(2-Ethyl-benzenesulfonyl)-5-nitro-quinolin-8-ylamine;
6-(2Isopropyl-benzenesulfonyl)-5-nitro-quinolin-8-ylamine;
6-(Naphthalene-1-sulfonyl)-5-nitro-quinolin- 8-ylamine;
6-(2Methoxy-benzenesulfonyl)-5-nitro-quinolin-8-ylamine;
6-(2,4-Dimethyl-benzenesulfonyl)-5-nitro-quinolin-8-ylamine;
6-(2,6-Dichloro-benzenesulfonyl)-5-nitro-quinolin-8-ylamine;
6-(2Bromo-benzenesulfonyl)-5-nitro-quinolin-8-ylamine;
N-[2-(8-Amino-5-nitro-quinoline-6-sulfonyl)-phenyl]-acetamide;
6-(2,3-Dichloro-benzenesulfonyl)-5-nitro-quinolin-8-ylamine;
6-(2-Fluoro-benzenesulfonyl)-5-nitro-quinolin-8-ylamine;
6-(2,6-Diisopropyl-benzenesulfonyl)-5-nitro-quinolin-8-ylamine;
5-Nitro-6-(2-trifluoromethyl-benzenesulfonyl)-quinolin-8-ylamine;
6-(2,5-Dichloro-benzenesulfonyl)-5-nitro-quinolin-8-ylamine; and
6-(2-tert-Butyl-benzenesulfonyl)-5-nitro-quinolin-8-ylamine.

4. A method of antagonizing neuropeptide Y comprising administering to a host a therapeutically effective amount of a compound according to claim 1 in unit dosage form.

5. A method of treating hypertension comprising administering to a host suffering therefrom a therapeutically effective amount of a compound according to Claim 1 in unit dosage form.

6. A pharmaceutical composition comprising a compound according to claim 1 in admixture with a pharmaceutically acceptable excipient, diluent, or carrier.

7. A pharmaceutical composition adapted for administration as an agent for treating obesity comprising a therapeutically effective amount of a compound according to claim 1 in admixture with a pharmaceutically acceptable excipient, diluent, or carrier.

8. A pharmaceutical composition adapted for administration as an agent for treating hypertension comprising a therapeutically effective amount of a compound according to claim 1 in admixture with a pharmaceutically acceptable excipient, diluent, or carrier.

9. A method for preparing a compound having the Formula I

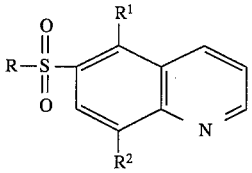

wherein R is aryl, or
$R^1$ is —$NO_2$,
—CN,
—$CO_2R^3$ wherein $R^3$ is H, alkyl, or aryl,
—$SO_2R^3$ wherein $R^3$ is as defined above,

wherein $R^3$ is as defined above,
or

wherein $R^3$ is as defined above;
$R^2$ is —$NH_2$,
—OH, or
—SH; with the exclusion of

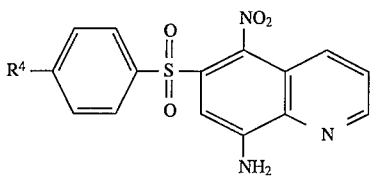

wherein $R^4$ is —$NH_2$ or

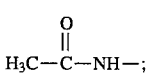

or a pharmaceutically acceptable salt thereof comprises reaction of a compound of Formula II

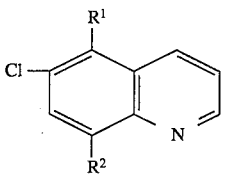

where $R^1$ and $R^2$ are as defined above with a compound of Formula III

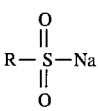

where R is as defined above in a solvent to afford a compound of Formula I and, if desired, converting a compound of Formula I to a corresponding pharmaceutically acceptable salt by conventional means and, if so desired, converting the corresponding pharmaceutically acceptable salt to a compound of Formula I by conventional means.

10. A method for preparing a compound having the Formula I

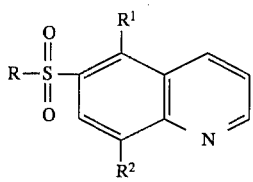

wherein R is aryl, or

R¹ is —NO₂,

—CN,

—CO₂R³ wherein R³ is H, alkyl, or aryl,

—SO₂R³ wherein R³ is as defined above

wherein R³ is as defined above, or

wherein R³ is as defined above;

R² is —NH₂,

—OH, or

—SH; with the exclusion of

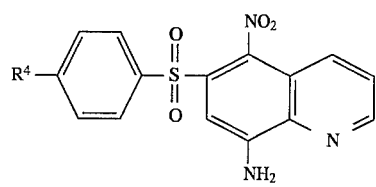

wherein R⁴ is —NH₂ or

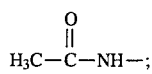

or a pharmaceutically acceptable salt thereof comprises reaction of a compound of Formula IV

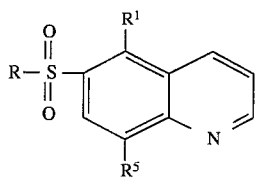

where R⁵ is

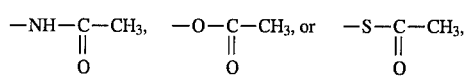

R and R¹ are as defined above with an acid to afford a compound of Formula I and, if desired, converting a compound of Formula I to a corresponding pharmaceutically acceptable salt by conventional means and, if so desired, converting the corresponding pharmaceutically acceptable salt to a compound of Formula I by conventional means.

* * * * *

UNITED STATES PATENT AND TRADEMARK OFFICE
CERTIFICATE OF CORRECTION

PATENT NO. : 5,552,411
DATED : September 3, 1996
INVENTOR(S) : Downing et al.

It is certified that error appears in the above-indentified patent and that said Letters Patent is hereby corrected as shown below:

Column 14, line 60 (Claim 2), insert --1- or 2-naphthyl,--

Signed and Sealed this

Seventeenth Day of April, 2001

Attest:

NICHOLAS P. GODICI

Attesting Officer     Acting Director of the United States Patent and Trademark Office